United States Patent
Neuhann et al.

(10) Patent No.: US 6,238,370 B1
(45) Date of Patent: May 29, 2001

(54) DEVICE FOR DILATING AND RESTORING THE LACRIMAL DUCT IN THE HUMAN EYE

(76) Inventors: Thomas Neuhann, Herzog Strasse 48, D-80801 Munich; Norbert Heske, Dorfstrasse 22a, D-82288 Kottgeisering; Jorg Hassel, Adalmund Strasse 32, D-82284 Grafrath, all of (DE)

( * ) Notice: Subject to any disclaimer, the term of this patent is extended or adjusted under 35 U.S.C. 154(b) by 0 days.

(21) Appl. No.: 09/463,482

(22) PCT Filed: May 27, 1999

(86) PCT No.: PCT/DE99/01561
§ 371 Date: Jan. 27, 2000
§ 102(e) Date: Jan. 27, 2000

(87) PCT Pub. No.: WO99/60962
PCT Pub. Date: Dec. 2, 1999

(30) Foreign Application Priority Data

May 27, 1997 (DE) .............................................. 198 23 755

(51) Int. Cl.⁷ ..................................................... A61M 29/00
(52) U.S. Cl. .............................................................. 604/104
(58) Field of Search ................................... 604/8–10, 96, 604/104, 264; 606/191, 108

(56) References Cited

U.S. PATENT DOCUMENTS

| | | | |
|---|---|---|---|
| 5,290,295 | * | 3/1994 | Querals . |
| 5,411,517 | * | 5/1995 | Guignard . |
| 5,437,625 | * | 8/1995 | Kurihashi . |
| 5,531,673 | * | 7/1996 | Helenowski . |
| 5,596,393 | * | 1/1997 | Trudell . |
| 6,083,188 | * | 7/2000 | Becker . |

* cited by examiner

Primary Examiner—Sharon Kennedy
Assistant Examiner—Catherine Serke
(74) Attorney, Agent, or Firm—Antonelli, Terry, Stout & Kraus, LLP

(57) ABSTRACT

What is described here is a device for dilating and restoring the lacrimal duct on the human eye, through which lacrimal fluid flows from the eye into the nasal cavity.

The inventive device is provided with the follow components:

a first hollow cannula with a distal end which presents at least one longitudinal gap, a guide passing through the first hollow cannula and having a distal end which dilates the distal end of the first cannula in the region of the gap, a hollow body surrounding the outside contour of the first hollow cannula in the distal zone, as well as a second hollow cannula adapted to be pushed over the first hollow cannula and extending up to the end on the proximal side of the hollow body, which is placed on the first hollow cannula so as to lock the latter and prevent it from axial sliding on the proximal side.

54 Claims, 4 Drawing Sheets

Fig. 1B
Fig. 1C
Fig. 1A
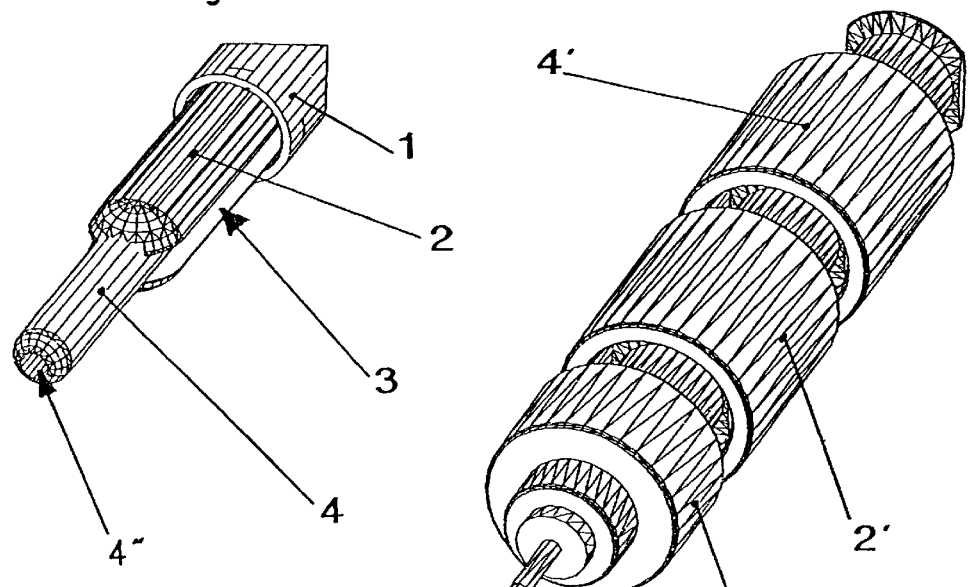
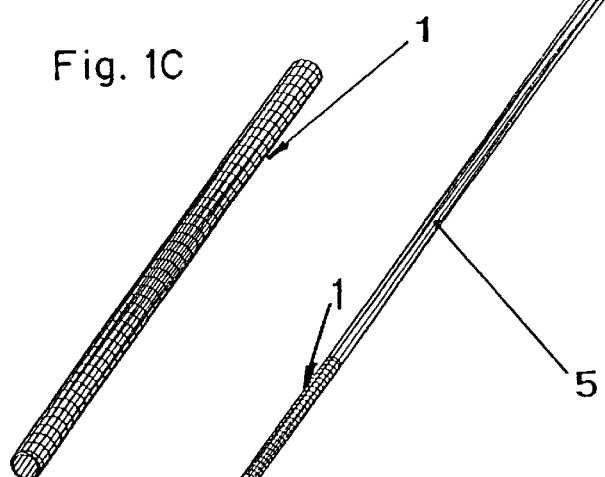
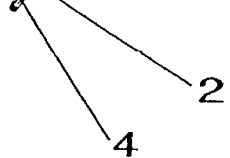

Fig. 3B
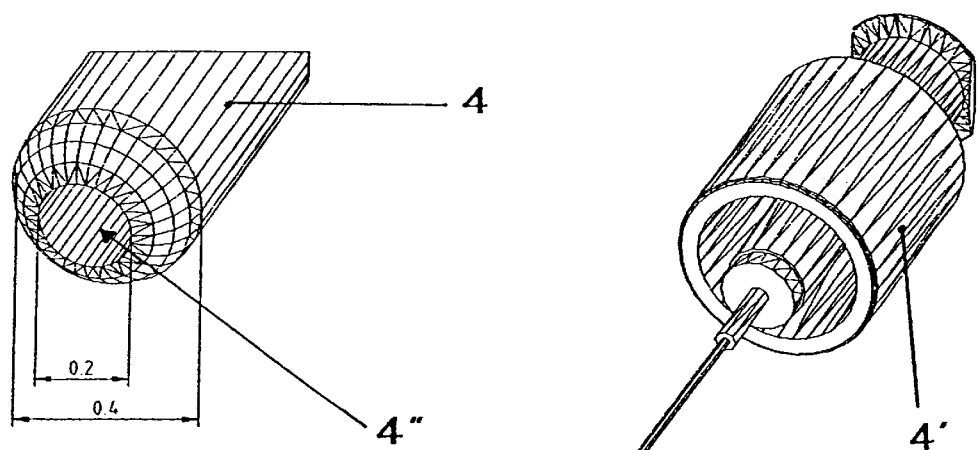
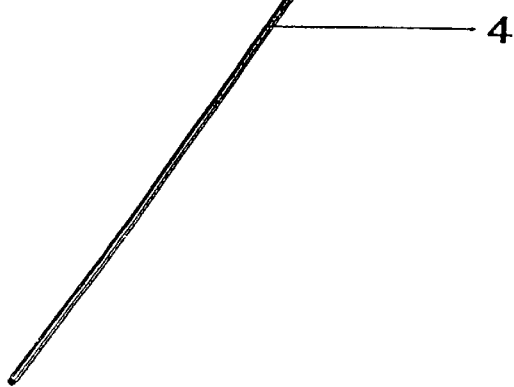
Fig. 3A

DEVICE FOR DILATING AND RESTORING THE LACRIMAL DUCT IN THE HUMAN EYE

BACKGROUND OF THE INVENTION

1. Field of the Invention

The present invention relates to a device for dilating and restoring the lacrimal duct in the human eye, through which lacrimal fluid flows from the eye into the nasal cavity.

2. Description of the Prior Art

In the human eye, lacrimal fluid serves not only to moisten the cornea surrounding the eye in the front zone and hence to avoid desiccation of the eye but has also a cleaning effect, for instance by washing out of the eye, so to speak, foreign bodies, bacteria or any other contaminants by means of the lacrimal fluid. Excess lacrimal fluid flows through the lacrimal duct, which is present on the nasal side at the eye, into the nasal cavity where the lacrimal fluid is evaporated and absorbed by the respiratory air and serves, for instance, to moisten the respiratory passages.

In cases where the lacrimal duct is partly or completely obstructed by internal adenoid infection or deposits, the natural outflow of lacrimal fluid is at least hindered or stopped completely. In such cases lacrimal fluid collects in the eye, preferably in the zone of the lower eyelids, with the formation of small stationary lakes of lacrimal fluid, so to speak, where contaminants may collect which constitute sources of infection for the eye cavity.

Such cases of insufficient outflow of lacrimal fluid occur, in particular, on elderly people, which can be treated either by medication and/or by surgery; in surgical operations the lacrimal duct is laid bare again even though it has so far not been possible to ensure that after the operation the lacrimal duct will not be obstructed again. Moreover, a surgical operation imposes a serious strain on the patient, which causes pain and particularly a long-lasting healing process and convalescence of the eye so that the patent's vision is restricted, at least temporarily.

SUMMARY OF THE INVENTION

The present invention is based on the problem of defining a device for dilating and restoring the lacrimal duct on the human eye, through which lacrimal fluid flows from the eye into the nasal cavity, of such a type that the strain on a patient to be treated can be substantially so reduced that an operation to be performed with the of the present invention device can take place in the outpatient department, without exposure of the patient to long-lasting complicated healing processes on the lacrimal duct to be treated as a result of traumatic irritation. The device should furthermore ensure that after performance of the operation the unrestricted function of the lacrimal duct will be restored and that moreover a repeated obstruction of the lacrimal duct will be largely precluded.

In accordance with the invention the device for dilating and restoring the lacrimal duct on the human eye, through which lacrimal fluid flows from the eye into the nasal cavity, is a cannula system presenting the following individual components:

A first hollow canal is provided on its distal end with at least one longitudinal cut. A guide, which is preferably configured as a hollow cannula in its turn, passes through the first hollow cannula and dilates the distal end of the first hollow cannula over which the longitudinal gap extends. Above the outside contour of the first hollow cannula a hollow body is provided, equally at the distal zone thereof, which surrounds the outside contour of the first hollow cannula and which is mounted thereon for displacement.

Finally, a second hollow cannula is provided which can be pushed over the first hollow cannula and which extends up to the end on the proximal side of the hollow body mounted on the fist hollow cannula, hence locking the second below cannula so as to prevent axial sliding on the proximal side.

The aforementioned individual components constitute a cannula system which allows firstly for a penetration into the lacrimal duct through the opening of the lacrimal duct present at the eye zone on the nasal side, and for dilating the obstructed lacrimal duct. An optical system for observation is preferably guided through the internal canal of the guide, and an irrigation canal is provided so that the operation of introducing the cannula system into the lacrimal duct can be visually observed and controlled on an appropriate transmission monitor, with the irrigating or through-drainage liquid exposing, on the one hand, the field of vision ahead of the tip of the cannula and supporting, on the other hand, the operation of penetration inside the lacrimal duct.

The device excels itself, however, particularly by the provision that a hollow body is provided on the distal end zone of the cannula system, which can be selectively introduced, together with the cannula system, into the lacrimal duct and can be fixed there. The cannula system is so designed that the hollow body, which is pushed onto the outer periphery of the first hollow cannula in the distal end zone, is fixed both in a direction towards the distal end and in a direction towards the proximal end of the cannula system. The proximal fixation is realized by means of the second hollow cannula which is pushed over the first cannula and which presents a bearing surfare on the distal side, against which the hollow body pushed onto the first hollow cannula bears by its end on the proximal side. The first hollow cannula is provided on the distal tip with a longitudinal gap for fixing the hollow body on the distal end of the cannula system, and presents preferably moreover an internal volume which tapers towards the distal tip. When the guide is inserted into the first hollow cannula the distal tip of the guide hits against the narrowing conical internal contour of the first hollow cannula, pressing the halves of the cannula apart on the distal tip so that the outer diameter of the first hollow cannula will be enlarged on the distal zone. The enlargement of the outer diameter is envisaged in such a way that the hollow body, which is seated on the first hollow cannula, cannot be pushed beyond the tip of the first hollow cannula. In this manner, the hollow body is locked and prevented from sliding on the first hollow cannula both on the distal and the proximal side. In this condition, the inventive cannula system of the present invention is introduced into the lacrimal duct to be treated until a desired position is reached inside the lacrimal duct so that, for instance, the hollow body, which is preferably configured as a metal spiral, will extend in the longitudinal direction over the entire lacrimal duct. In this position, the internal guide is removed from the first hollow cannula, which causes the retraction of the distal dilation to the normal diameter of the hollow cannula. In a further step, the first hollow cannula is retracted relative to the second hollow cannula, while the hollow body, which is seated on the first hollow cannula in the form of a metal spiral, remains at the envisaged site inside the lacrimal duct, specifically since the hollow body is locked by the second hollow cannula and protected from sliding on the proximal side, which may be induced when the first hollow cannula is retracted. Only upon the complete removal of the first hollow cannula from the second hollow cannula it is possible to remove the second hollow cannula as well from the lacrimal duct so that merely the hollow body introduced into the lacrimal duct will fixedly be retained therein.

Immediately upon removal of the first hollow cannula, it is moreover possible to introduce an observation endoscope through the second hollow cannula, which is placed in the lacrimal duct, for checking the hollow body for correct seating in the lacrimal duct. In the event of a subsequent correction the first hollow cannula must then be inserted through the second hollow cannula into the lacrimal duct and subsequently the guide must be introduced into the first hollow cannula so that the hollow body will be locked in both directions for protection from sliding along the hollow cannula. In this state the hollow body must be re-adjusted relative to the lacrimal duct so that the aforedescribed procedure of removal of the cannula system may be performed after adjustment.

The use of a metal spiral as a hollow body has turned out to be particularly expedient, specifically since the metal spiral allows for proper fixation within the tissue in the lacrimal duct on account of its wavy surface. It is moreover to improve both the inflow from the lacrimal sac into the lacrimal duct and the outflow into the nasal sac when the windings of the metal spiral on the respective end of the spiral are extended. As a matter of fact the metal spiral is axially flexible so that curvatures in the lacrimal duct can be overcome at any time or may be adapted to them, respectively. Other embodiments of the hollow body are, of course, conceivable as well, for instance small elastic tubes which are made of synthetic material, preferably PMMA or silicone compositions.

BRIEF DESCRIPTION OF THE DRAWING

The invention will be described in the following, without any restriction of the general inventive idea, by the example of embodiments with reference to the drawing wherein:

FIG. 1 is a perspective view of the cannula system as a whole,

FIG. 3 illustrates the guide, and

BRIEF DESCRIPTION OF A PREFERRED EMBODIMENT

Figure 2:
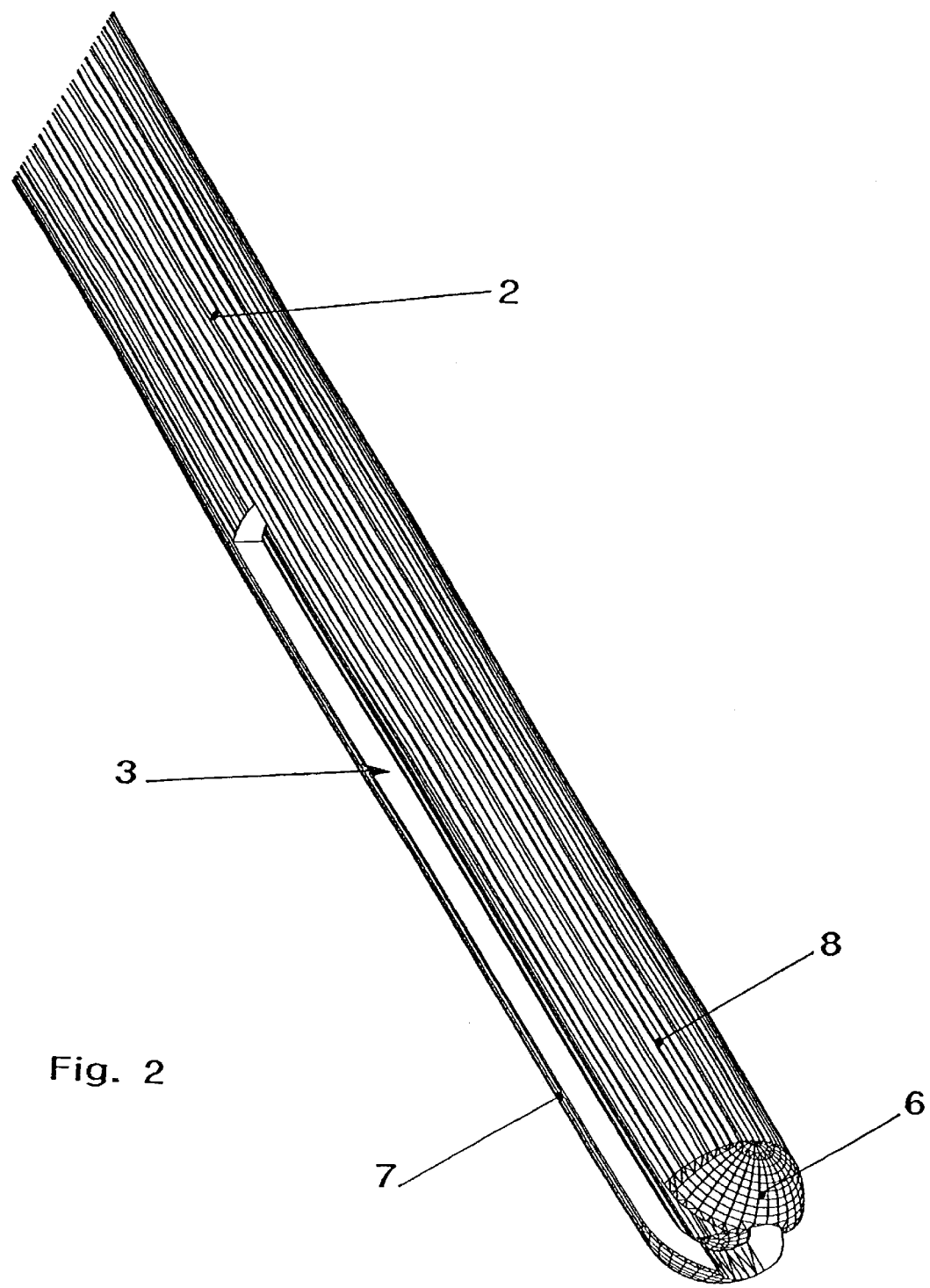
FIG. 2 shows the distal zone of the first hollow cannula.

FIG. 1 is a perspective view of the complete cannula system for dilating and restoring a lacrimal duct on the human eye. A hollow body 1, which is preferably configured as metal spiral, is seated on the outside contour of a first hollow cannula 2 which presents a longitudinal gap 3 on its distal end (cf. in this respect particularly the detail view in FIG. 1). A guide 4 is pushed through the interior of the first hollow cannula 2, which has firstly an inside hollow canal 4" through which an optical observation system and/or an irrigation canal may be passed, for instance. Moreover, a second hollow cannula 5 is pushed over the first hollow cannula 2, which has a longitudinal extension so dimensioned that the end of the second hollow cannula 5 on the distal side abuts against the end of the hollow body 1 on the proximal side, which body is seated on the distal side of the hollow cannula 2. The individual hollow cannulae or the guide, respectively, are connected to appropriate manipulating or grip elements on the proximal side. In correspondence with the illustration in FIG. 1, the reference numeral 5' denotes the grip end of the second hollow cannula, numeral 4' indicates the grip end of the guide, and numeral 2' refers to the grip end of the first hollow cannula.

The respective inside or outside diameters of the two hollow cannulae 2 and 5, of the guide 4 as well as of the hollow body 1 are so matched with each other that the individual components may slide relative to or on each other, respectively.

FIG. 2 shows the distal zone of the first hollow cannula 2, which is provided with a longitudinal gap 3. In particular, the distal tip 6 of the first hollow cannula 2 is beaded or crimped in such a way that the inner diameter of the hollow cannula tapers conically towards the distal tip. When the guide 4, which is not shown in FIG. 2, is pushed through the hollow cannula 2, the guide 4 hits against the narrowing inner contour of the distal tip 6 and spreads the upper and lower halves 7 and 8 of the cannula apart. As a result, the outer diameter of the first hollow cannula 2 is enlarged at the distal tip thereof so that the hollow body, which is seated on the hollow cannula 2, cannot be displaced beyond the distal tip 6.

FIG. 3 illustrates the guide 4 with an associated grip end 4'. In the detailed view according to FIG. 3 a hollow canal 4' can be seen through which an optical observation endoscope system in the form of a glass fibre and/or a canal provided with irrigating fluid may be passed, as has been set out in the foregoing already.

Figures 4A, 4B:
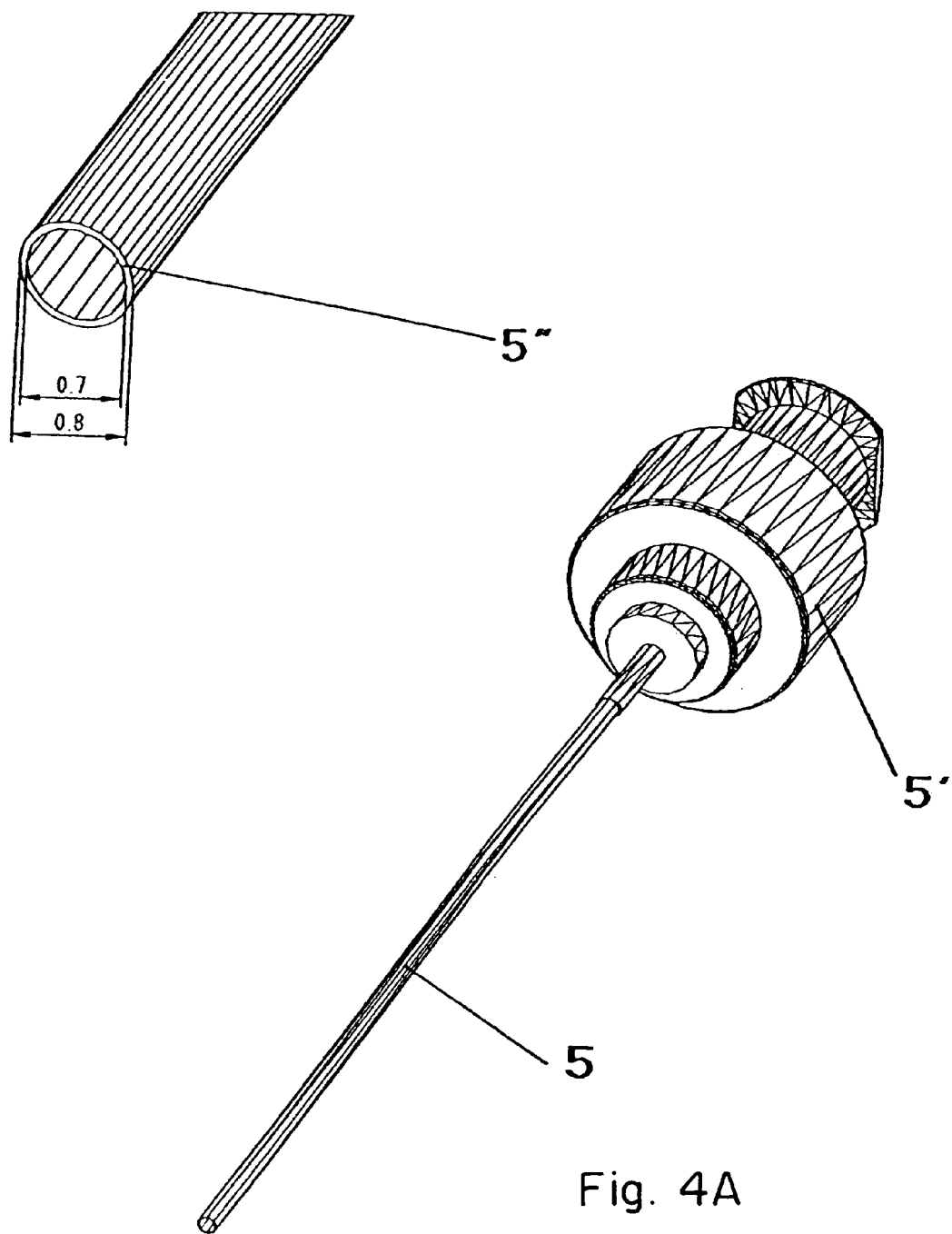
FIG. 4 shows the second hollow cannula.

Finally, FIG. 4 illustrates the second hollow cannula 5 with an associated grip end 5', which has an inner diameter so dimensioned that a sliding movement on the first hollow cannula 2 is possible. Furthermore, in correspondence with the detail view in FIG. 4, the second hollow cannula 5 is provided with a bearing surface 5" on the distal side, against which the hollow body 1 bears by its proximal end.

The hollow body 1 is preferably made of a special steel which, by the way, all the other elements of the cannula are made from. It is also conceivable to use nickel/titanium alloys for the individual components.

LIST OF REFERENCE NUMERALS 1 hollow body
2 first hollow cannula
2' grip end of the first hollow cannula
3 longitudinal gap
4 guide
4' grip end of the guide
4" hollow canal
5 second hollow cannula
5' grip end of the second hollow cannula
5" bearing surface
6 distal tip
7,8 lower and upper halves of the hollow cannula at the longitudinal gap

What is claimed is:

1. A device for dilating and restoring a lacrimal duct of a human eye, through which lacrimal fluid flows from the eye into a nasal cavity, comprising:
   a first hollow cannula with a distal end having at least one longitudinal gap;
   a guide passing through the first hollow cannula and having a distal end which dilates the distal end of the first cannula in a region of the at least one longitudinal gap;
   a hollow body surrounding an outside contour of the first hollow cannula in a distal zone; and
   a second hollow cannula which is pushed over the first hollow cannula and extends up to an end on a proximal side of the hollow body, which is placed on the first hollow cannula to lock the first hollow cannula and prevent axial sliding thereof on the proximal side.

2. The device according to claim 1, wherein:
the distal end of the first hollow cannula is provided with a zone which narrows an inner diameter of the first hollow cannula.

3. The device according to claim 2, wherein:
the zone conically narrows the inner diameter of the first hollow cannula.

4. The device according to claim 1, wherein:
a distal tip of the first hollow cannula is deformed to cause an inner diameter thereof to be smaller than an outer diameter of the guide.

5. The device according to claim 2, wherein:
a distal tip of the first hollow cannula is deformed to cause an inner diameter thereof to be smaller than an outer diameter of the guide.

6. The device according to claim 3, wherein:
a distal tip of the first hollow cannula is deformed to cause an inner diameter thereof to be smaller than an outer diameter of the guide.

7. The device according to claim 1, wherein:
the guide comprises at least one hollow canal providing a passage of at least one of an optical observation system and an irrigation canal.

8. The device according to claim 2, wherein:
the guide comprises at least one hollow canal providing a passage of at least one of an optical observation system and an irrigation canal.

9. The device according to claim 3, wherein:
the guide comprises at least one hollow canal providing a passage of at least one of an optical observation system and an irrigation canal.

10. The device according to claim 4, wherein:
the guide comprises at least one hollow canal providing a passage of at least one of an optical observation system and an irrigation canal.

11. The device according to claim 5, wherein:
the guide comprises at least one hollow canal providing a passage of at least one of an optical observation system and an irrigation canal.

12. The device according to claim 6, wherein:
the guide comprises at least one hollow canal providing a passage of at least one of an optical observation system and an irrigation canal.

13. The device according to claim 1, wherein:
the hollow body is a metal spiral having an inner diameter corresponding at least to an outer diameter of the first hollow cannula and is configured to be pushed along the outside contour of the first hollow cannula.

14. The device according to claim 2, wherein:
the hollow body is a metal spiral having an inner diameter corresponding at least to an outer diameter of the first hollow cannula and is configured to be pushed along the outside contour of the first hollow cannula.

15. The device according to claim 3, wherein:
the hollow body is a metal spiral having an inner diameter corresponding at least to an outer diameter of the first hollow cannula and is configured to be pushed along the outside contour of the first hollow cannula.

16. The device according to claim 4, wherein:
the hollow body is a metal spiral having an inner diameter corresponding at least to an outer diameter of the first hollow cannula and is configured to be pushed along the outside contour of the first hollow cannula.

17. The device according to claim 5, wherein:
the hollow body is a metal spiral having an inner diameter corresponding at least to an outer diameter of the first hollow cannula and is configured to be pushed along the outside contour of the first hollow cannula.

18. The device according to claim 6, wherein:
the hollow body is a metal spiral having an inner diameter corresponding at least to an outer diameter of the first hollow cannula and is configured to be pushed along the outside contour of the first hollow cannula.

19. The device according to claim 7, wherein:
the hollow body is a metal spiral having an inner diameter corresponding at least to an outer diameter of the first hollow cannula and is configured to be pushed along the outside contour of the first hollow cannula.

20. The device according to claim 8, wherein:
the hollow body is a metal spiral having an inner diameter corresponding at least to an outer diameter of the first hollow cannula and is configured to be pushed along the outside contour of the first hollow canhula.

21. The device according to claim 9, wherein:
the hollow body is a metal spiral having an inner diameter corresponding at least to an outer diameter of the first hollow cannula and is configured to be pushed along the outside contour of the first hollow cannula.

22. The device according to claim 10, wherein:
the hollow body is a metal spiral having an inner diameter corresponding at least to an outer diameter of the first hollow cannula and is configured to be pushed along the outside contour of the first hollow cannula.

23. The device according to claim 11, wherein:
the hollow body is a metal spiral having an inner diameter corresponding at least to an outer diameter of the first hollow cannula and is configured to be pushed along the outside contour of the first hollow cannula.

24. The device according to claim 12, wherein:
the hollow body is a metal spiral having an inner diameter corresponding at least to an outer diameter of the first hollow cannula and is configured to be pushed along the outside contour of the first hollow cannula.

25. The device according to claim 1, wherein:
the hollow body has a length which is not greater than a length of the lacrimal duct to be treated.

26. The device according to claim 2, wherein:
the hollow body has a length which is not greater than a length of the lacrimal duct to be treated.

27. The device according to claim 4, wherein:
the hollow body has a length which is not greater than a length of the lacrimal duct to be treated.

28. The device according to claim 7, wherein:
the hollow body has a length which is not greater than a length of the lacrimal duct to be treated.

29. The device according to claim 13, wherein:
the hollow body has a length which is not greater than a length of the lacrimal duct to be treated.

30. The device according to claim 1, wherein:
the second hollow cannula has an annular bearing surface on a distal tip thereof, against which a contour of the hollow body at a proximal side thereof bears.

31. The device according to claim 2, wherein:
the second hollow cannula has an annular bearing surface on a distal tip thereof, against which a contour of the hollow body at a proximal side thereof bears.

32. The device according to claim 3, wherein:
the second hollow cannula has an annular bearing surface on a distal tip thereof, against which a contour of the hollow body at a proximal side thereof bears.

33. The device according to claim 4, wherein:
the second hollow cannula has an annular bearing surface on a distal tip thereof, against which a contour of the hollow body at a proximal side thereof bears.

34. The device according to claim 7, wherein:
the second hollow cannula has an annular bearing surface on a distal tip thereof, against which a contour of the hollow body at a proximal side thereof bears.

35. The device according to claim 13, wherein:
the second hollow cannula has an annular bearing surface on a distal tip thereof, against which a contour of the hollow body at a proximal side thereof bears.

36. The device according to claim 25, wherein:
the second hollow cannula has an annular bearing surface on a distal tip thereof, against which a contour of the hollow body at a proximal side thereof bears.

37. The device according to claim 1, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

38. The device according to claim 2, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

39. The device according to claim 3, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

40. The device according to claim 4, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

41. The device according to claim 7, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

42. The device according to claim 13, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

43. The device according to claim 25, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

44. The device according to claim 30, wherein:
a dilation of the distal end of the first hollow cannula causes an outer diameter of a distal tip of the first hollow cannula to be wider than an inner diameter of the hollow body so that sliding of the hollow body on the first hollow cannula towards the distal end is prevented, and when the guide is removed from the first hollow cannula, dilation of the distal end is reduced to an original outer diameter of the first hollow cannula so that the hollow body can be placed on the distal end.

45. The device according to claim 1, wherein:
an outer diameter of the second hollow cannula is approximately 0.8 mm.

46. The device according to claim 13, wherein:
the metal spiral is flared at ends thereof to provide an increased spacing of windings at the ends thereof relative to spacing of windings of the metal spiral inboard of the order thereof.

47. The device according to claim 1, wherein:
the hollow body has an inner diameter corresponding to an outer diameter of the first hollow cannula and which is configured to be pushed onto an outer contour of the first hollow cannula.

48. The device according to claim 2, wherein:
the hollow body has an inner diameter corresponding to an outer diameter of the first hollow cannula and which is configured to be pushed onto an outer contour of the first hollow cannula.

49. The device according to claim 3, wherein:
the hollow body has an inner diameter corresponding to an outer diameter of the first hollow cannula and which is configured to be pushed onto an outer contour of the first hollow cannula.

50. The device according to claim 4, wherein:
the hollow body has an inner diameter corresponding to an outer diameter of the first hollow cannula and which is configured to be pushed onto an outer contour of the first hollow cannula.

51. The device according to claim 7, wherein:

the hollow body has an inner diameter corresponding to an outer diameter of the first hollow cannula and which is configured to be pushed onto an outer contour of the first hollow cannula.

52. The device according to claim 47, wherein:

the hollow body is a synthetic material.

53. The device of claim 52, wherein:

the synthetic material is PMMA.

54. The device of claim 52, wherein:

the synthetic material is a silicone composition.

* * * * *